United States Patent [19]

Worschech et al.

[11] 4,338,226

[45] Jul. 6, 1982

[54] PROCESS FOR THE STABILIZATION OF POLYVINYL CHLORIDE AND STABILIZER COMPOSITIONS

[75] Inventors: Kurt Worschech, Loxstedt; Peter Wedl, Loxstedt-Bexhövede; Frido Löffelholz, Bremerhaven; Bernd Wegemund, Haan; Werner Erwied, Langenfeld, all of Fed. Rep. of Germany

[73] Assignee: Neynaber Chemie GmbH, Loxstedt, Fed. Rep. of Germany

[21] Appl. No.: 194,851

[22] Filed: Oct. 7, 1980

[30] Foreign Application Priority Data

Oct. 13, 1979 [DE] Fed. Rep. of Germany ....... 2941597
Jun. 16, 1980 [AT] Austria ................................ 3168/80

[51] Int. Cl.³ .............................................. C08K 5/09
[52] U.S. Cl. ..................................... 524/302; 524/305; 524/569; 524/450
[58] Field of Search .......... 260/23 XA, 31.6, 45.85 H, 260/42.49

[56] References Cited

U.S. PATENT DOCUMENTS

| | | |
|---|---|---|
| 4,000,100 | 12/1976 | Baldyga ............................ 260/42.54 |
| 4,178,282 | 12/1979 | Bae .................................. 260/45.75 W |
| 4,202,806 | 5/1980 | Yoshida .......................... 260/23 XA |
| 4,220,570 | 9/1980 | Loffelholz .......................... 260/31.6 |

*Primary Examiner*—Paul R. Michl
*Attorney, Agent, or Firm*—Hammond & Littell, Weissenberger and Muserlian

[57] ABSTRACT

This invention is directed to a process for stabilizing polyvinyl chloride molding mixtures which comprises admixing (a) from about 0.2 to 5 parts by weight of a sodium aluminosilicate of small particle size;
(b) from about 0.05 to 1.5 parts by weight of one or more calcium salts of fatty acids;
(c) from about 0.05 to 0.5 parts by weight of one or more zinc salts of fatty acids;
(d) from about 0.2 to 2.0 parts by weight of partial esters of polyols and fatty acids; and
(e) from about 0.1 to 10 parts by weight of thioglycolic acid esters of polyols and/or thioglycolic acid esters of monofunctional alcohols per 100 parts by weight of polyvinyl chloride or copolymer of vinyl chloride.

26 Claims, No Drawings

PROCESS FOR THE STABILIZATION OF POLYVINYL CHLORIDE AND STABILIZER COMPOSITIONS

FIELD OF THE INVENTION

This invention is directed to the stabilization of polyvinyl chloride molding mixtures. More particularly, this invention is directed to a process for stabilizing molding mixtures based upon polyvinyl chloride or vinyl chloride copolymers which comprises adding thereto alkali metal aluminosilicates, calcium and zinc salts of fatty acids, partial esters of polyols and fatty acids, and polyols and/or thioglycolates.

BACKGROUND OF THE INVENTION

Lead, tin, barium or cadmium compounds are predominantly used as stabilizers in the manufacture of polyvinyl chloride articles. These heavy metal stabilizers have a very satisfactory effect in practice; however, certain doubts exist concerning their use, particularly with respect to occupational physiology, i.e., toxicology. For this reason, attempts have been made for a long time to replace the normally used heavy metal stabilizers with less objectionable substances. The use of soaps of the light alkaline earth metals in place of the heavy metal stabilizers has already been suggested. In this regard, the use of calcium soaps is preferred, which use may be supplemented with co-stabilizers such as zinc stearate, imino compounds, or epoxy compounds, if desired.

The stabilizing effect of the calcium soap system is comparatively minor in comparison to that of the heavy metal compounds. Molded articles manufactured with the use of a stabilizer system based on calcium soaps frequently exhibit dark discolorations and have a low reserve stability. Consequently, the scope of application of such stabilizer systems is quite limited.

In U.S. Patent Application Ser. No. 834,515, filed Sept. 19, 1977, U.S. Pat. No. 4,220,570, 6-23-81 a stabilizer combination is described which contains a partial ester of pentaerythritol with a fatty acid having from 12 to 22 carbon atoms, a waxy hydrocarbon and/or a free fatty acid having from 12 to 22 carbon atoms, calcium stearate and/or zinc stearate, as well as an antioxidant. However, this combination is not as effective as stabilizer systems based upon heavy metal compounds.

In U.S. Pat. No. 4,000,100 the use of so-called nonactivated zeolite A in stabilizer systems for resin compounds based upon polyvinyl chloride, is disclosed. A significant aspect of the teaching of this reference is the realization that by incorporation of certain water-containing zeolite types in stabilizer systems, synergistic action increases with respect to thermal and light protection can be achieved. The zeolites proposed for this purpose are those of types 3A, 4A, and 5A. They are to be used with any desired inorganic, organometallic, or organic stabilizers or stabilizer components.

Thus, there has remained the need to improve the stabilization of polyvinyl chloride with the aid of combinations based on calcium and, if desired, zinc soaps in such a manner that the production of polyvinyl chloride articles with a light pigmentation or a white color and satisfactory reserve stability becomes possible without the use of lead, tin, barium, or cadmium compounds.

OBJECTS OF THE INVENTION

It is an object of the present invention to develop a stabilizer combination for addition to moldable compositions based upon polyvinyl chloride or vinyl chloride copolymers, which combination gives a readily shapable, moldable composition which when molded has good initial color, long time stability under thermal stress, and low toxicity.

It is also an object of the invention to stabilize molding compositions based upon polyvinyl chloride by incorporating therein, per 100 parts of polymer, (a) from about 0.2 to 5 parts by weight of a synthetic, crystalline sodium aluminosilicate of small particle size and containing from about 13 to 25 percent by weight of water of crystallization, which has the composition $$0.7-1.1 Na_2O \cdot Al_2O_3 \cdot 1.3-2.4 SiO_2$$

with respect to the anhydrous form;

(b) from about 0.05 to 1.5 parts by weight of one or more calcium salts of fatty acids with from 8 to 22 carbon atoms;

(c) from about 0.05 to 0.5 parts by weight of one or more zinc salts of fatty acids with from 8 to 22 carbon atoms;

(d) from about 0.2 to 2.0 parts by weight of partial esters of polyols with from 2 to 6 carbon atoms and from 2 to 6 hydroxyl groups and fatty acids with from 8 to 22 carbon atoms, which contain an average of at least one free polyol-hydroxyl group per molecule; and (e) from about 0.1 to 10 parts by weight of thioglycolic acid esters of polyols with
   from 2 to 6 hydroxyl groups and/or thioglycolic acid esters of monofunctional alcohols with from 8 to 22 carbon atoms.

It is a further object of the invention to develop a stabilizer combination for molding compositions based upon polyvinyl chloride or vinyl chloride copolymers which comprises (a) from about 4 to 100 parts by weight of a synthetic, crystalline sodium aluminosilicate of small particle size and containing from about 13 to 25 percent by weight of water of crystallization, which has the composition $$0.7-1.1 Na_2O \cdot Al_2O_3 \cdot 1.3-2.4 SiO_2$$

with respect to the anhydrous form;

(b) from about 1 to 30 parts by weight of one or more calcium salts of fatty acids with from 8 to 22 carbon atoms;

(c) from about 1 to 10 parts by weight of one or more zinc salts of fatty acids with from 8 to 22 carbon atoms;

(d) from about 4 to 40 parts by weight of partial esters of polyols with from 2 to 6 carbon atoms and from 2 to 6 hydroxyl groups and fatty acids with from 8 to 22 carbon atoms, which contain an average of at least one free polyol-hydroxyl group per molecule; and (e) from about 2 to 20 parts by weight of thioglycolic acid esters of polyols with
   from 2 to 6 hydroxyl groups and/or thioglycolic acid esters of monofunctional alcohols with from 8 to 22 carbon atoms.

These and other objects of the invention will become more apparent in the description below.

DETAILED DESCRIPTION OF THE INVENTION

It has surprisingly been found that the desired improvement in the stabilization of polyvinyl chloride compounds can be achieved by the selection and combination of a plurality of certain components, including the selection of a certain aluminosilicate of the zeolite type. More specifically, the invention herein relates to a process for the stabilization of polyvinyl chloride molding mixtures, which is characterized by the fact that per 100 parts of polymer, (a) from about 0.2 to 5 parts by weight of a synthetic, crystalline sodium aluminosilicate of small particle size and containing from about 13 to 25 percent by weight of water of crystallization, which has the composition $$0.7{-}1.1Na_2O.Al_2O_3.1.3{-}2.4SiO_2$$

with respect to the anhydrous form;

(b) from about 0.05 to 1.5 parts by weight of one or more calcium salts of fatty acids with from 8 to 22 carbon atoms;

(c) from about 0.05 to 0.5 parts by weight of one or more zinc salts of fatty acids with from 8 to 22 carbon atoms;

(d) from about 0.2 to 2.0 parts by weight of partial esters of polyols with from 2 to 6 carbon atoms and from 2 to 6 hydroxyl groups and fatty acids with from 8 to 22 carbon atoms, which contain an average of at least one free polyol-hydroxyl group per molecule; and (e) from about 0.1 to 10 parts by weight of thioglycolic acid esters of polyols with from 2 to 6 carbon atoms and from 2 to 6 hydroxyl groups and/or thioglycolic acid esters of monofunctional alcohols with from 8 to 22 carbon atoms are worked into the molding mixture.

In a preferred embodiment of the invention, a total of from about 1 to 10 parts by weight, most preferably from about 2 to 5 parts by weight, of components (a) to (e) are added per 100 parts by weight of polyvinyl chloride or copolymer of vinyl chloride.

The invention herein also relates to a stabilizer combination comprising:

(a) from about 4 to 100 parts by weight of a synthetic, crystalline sodium aluminosilicate of small particle size and containing from about 13 to 25 percent by weight of water of crystallization, which has the composition $$0.7{-}1.1Na_2O.Al_2O_3.1.3{-}2.4SiO_2$$

with respect to the anhydrous form;

(b) from about 1 to 30 parts by weight of one or more calcium salts of fatty acids with from 8 to 22 carbon atoms;

(c) from about 1 to 10 parts by weight of one or more zinc salts of fatty acids with from 8 to 22 carbon atoms;

(d) from about 4 to 40 parts by weight of partial esters of polyols with from 2 to 6 carbon atoms and from 2 to 6 hydroxyl groups and fatty acids with from 8 to 22 carbon atoms, which contain an average of at least one free polyol-hydroxyl group per molecule; and (e) from about 2 to 20 parts by weight of thioglycolic acid esters of polyols with from 2 to 6 hydroxyl groups and/or thioglycolic acid esters of monofunctional alcohols with from 8 to 22 carbon atoms.

A further aspect of the invention is the articles prepared from polyvinyl chloride-based resin compounds stabilized according to the invention. This comprises both the correspondingly stabilized molding mixtures as such, as well as the resulting molded bodies resulting from a desired molding or shaping procedure.

The above-defined synthetic, crystalline sodium aluminosilicates are known zeolites of the type NaA that possess an average effective pore diameter of 4 Å, for which reason they are also called zeolites 4A. Such sodium aluminosilicates can be prepared by known methods. Suitable syntheses are described, for example, in U.S. patent application Ser. No. 458,306, filed Apr. 5, 1974, now abandoned in favor of continuation application Ser. No. 800,308, filed May 25, 1977, now abandoned in favor of continuation-in-part application Ser. No. 956,851, filed Nov. 2, 1978. Further details concerning the nature and production of these aluminosilicates can be found, for example, in the following references: German Published Applications (DE-OS) Nos. 26 41 485, 26 51 455, 26 51 436, 26 51 419, 26 51 420, and 26 51 437, and U.S. Pat. No. 3,112,176, incorporated herein by reference.

The sodium aluminosilicates produced by precipitation and present in the form of a finely dispersed suspension can be converted from the amorphous to the crystalline state by heating to temperatures of from about 50° to 200° C. Then, the crystalline sodium aluminosilicate can be separated from the remaining aqueous solution by filtration and usually dried at temperatures of, for example, 50° to 200° C., until the water content is from about 13 to 25 percent by weight.

The crystalline products described in U.S. patent application Ser. No. 458,306 and used herein according to the invention have a particle size in the range from about 0.1 to 50μ. Sodium aluminosilicates with a particle size of from about 0.1 to 20μ are preferably used for the performance of the process according to the invention. The calcium binding capacity of the sodium aluminosilicates, determined at 22° C., is at least 50 mg CaO/g anhydrous active substance and may attain values of about 200 mg CaO/g active substance. Preferably this calcium binding capacity is in the range of about 100 to 200 mg CaO/g active substance, being normally in the range of above 150 mg CaO/g. Details concerning the determination of the calcium binding capacity can be found in U.S. patent application Ser. No. 458,306 as well as in the text below.

Sodium aluminosilicates with rounded corners and edges also may be used in a preferred embodiment of the process according to the invention. The preparation of such zeolites begins advantageously with a batch having a molar composition in the range $$2.5{-}6.0Na_2O.Al_2O_3.0.5{-}5.0SiO_2.60{-}200H_2O.$$

This preparation is crystallized in a conventional manner. Advantageously, this is effected by heating the preparation for at least ½ hour at from 70° to 120° C., preferably at from 80° to 95° C., under agitation. The crystalline product is isolated in a simple manner by separating the liquid phase. If required, it is advisable to re-wash the products with water and to dry them before further processing.

Those sodium aluminosilicates of small particle size that are insoluble in water and were precipitated and crystallized in the presence of water-soluble, inorganic or organic dispersing agents, may also be used in the process according to the invention. Products of this type are described in U.S. Patent Applications Ser. No.

503,467, filed Sept. 5, 1974, now abandoned; Ser. No. 763,667, filed Jan. 28, 1977, now abandoned; and Ser. No. 811,964, filed June 30, 1977, now U.S. Pat. No. 4,126,574. They are obtainable in a technically simple manner. Suitable water-soluble organic dispersing agents include tensides, non-surface-active aromatic sulfonic acids, and compounds having a complex-forming capacity for calcium. The dispersing agents may be introduced into the reaction mixture in a desired manner, before or during precipitation, and they may be introduced, for example, in the form of a solution or they may be dissolved in the aluminate solution and/or silicate solution. Particularly satisfactory effects are obtained when the dispersing agent is dissolved in the silicate solution. The quantity of dispersing agent should be at least about 0.05 percent by weight, preferably from about 0.1 to 5 percent by weight, based on the total amount of precipitate obtained. The product of precipitation is heated to temperatures of from 50° to 200° C. for from ½ to 24 hours for the crystallization. Examples of suitable dispersing agents include sodium lauryl ether sulfate, sodium polyacrylate, and the sodium salts of 1-hydroxy-ethane-1,1-diphosphonic acid.

The sodium aluminosilicates of the type NaA suitable for the performance of the process according to the invention contain from about 13 to 25 percent by weight of water of crystallization. Products with a water content in the range from about 18 to 25 percent by weight are preferably used.

The calcium and zinc salts of fatty acids used in the process according to the invention are preferably derived from the fatty acids such as, for example, caprylic, caproic, lauric, myristic, palmitic, and stearic acid. Useful salts include salts of single fatty acids as well as salts of mixtures of fatty acids such as are obtained from natural fats and oils. The use of calcium or zinc salts of saturated fatty acids such as palmitic and/or stearic acid is preferred.

The polyol partial esters of component (d) are prepared in a known manner by esterification of polyols with from 2 to 6 carbon atoms and from 2 to 6 hydroxyl groups with fatty acids with a chain length of from 8 to 22 carbon atoms, in which process conventional esterification catalysts may also be used. For this purpose, polyols and fatty acids are reacted at a molar ratio of from 1:1 to 1:(n-1), n standing for the number of hydroxyl groups in the polyol. The reaction partners are advantageously used in amounts such that partial esters with an OH-number of from about 140 to 580, preferably from about 170 to 540, are formed. The reaction product, which represents a mixture of different esters, should have an acid number less than 15, preferably less than 8.

Suitable polyol components are, for example, ethylene glycol, 1,2-propylene glycol, 1,3-propylene glycol, 1,2-butylene glycol, 1,4-butylene glycol, 1,6-hexanediol, neopentyl glycol, glycerol, trimethylolethane, trimethylolpropane, pentaerythritol, erythritol, mannitol, and sorbitol. Particularly significant polyol components have from 3 to 6 hydroxyl groups, preferably 3 to 4 hydroxyl groups. In the context of the invention herein, the use of glycerol or pentaerythritol is particularly advantageous. Caprylic, caproic, lauric, myristic, palmitic, stearic, and behenic acid are examples of suitable fatty acid components. Synthetic fatty acids of the above-mentioned chain length, such as mineral acids, unsaturated acids such as oleic acid and linolenic acid, and substituted fatty acids, particularly 12-hydroxystearic acid, may also be used. For practical reasons, mixtures of fatty acids from natural fats and oils are used most frequently. Component (d) may also consist of a mixture of the above-mentioned partial esters. Especially preferred compounds of component (d) may comprise partial esters of polyols with from 3 to 6 hydroxyl groups, preferably 3 to 4 hydroxyl groups, and the fatty acids discussed, the partial esters having an average of from 2 to 3 free hydroxyl groups.

Suitable substances for component (e) include in one embodiment of the invention thioglycolic acid esters of aliphatic polyols with from 2 to 6 hydroxyl groups. These polyols contain preferably from 2 to 36 carbon atoms, especially from 2 to 18 carbon atoms. Examples of polyols having from 2 to 6 carbon atoms include ethylene glycol, 1,2-propylene glycol, 1,3-propylene glycol, 1,2-butylene glycol, 1,4-butylene glycol, 1,6-hexanediol, neopentyl glycol, glycerol, trimethylol ethane, trimethylol propane, pentaerythritol, mannitol, and sorbitol. Polyols having a higher carbon atom number within the given range, e.g. from 8 to 18 carbon atoms, are also particularly suitable. Preferred polyols in one embodiment of the invention are those having from 2 to 4 hydroxyl groups, especially ethylene glycol, glycerine and pentaerythritol. $\alpha,\omega$-alkanediols having from 8 to 18 carbon atoms, such as 1,10-decanediol, 1,12-dodecanediol and 1,18-octadecanediole are also especially suitable polyols. A further group of suitable compounds includes diols or polyols which may be obtained by hydrolysis of long-chain epoxy alkanes. These diols or polyols contain the vicinal hydroxyl groups in terminal or non-terminal position. Within this group compounds having from 8 to 18 carbon atoms are preferred, e.g. 1,2-octanediol, 1,2-decanediol, 1,2-tetradecanediol, 1,2-octadecanediol, mixtures of vicinal alcanediols with the OH groups in random distribution in non-terminal positions having a carbon chain length of $C_{12}$ or $C_{14}$ or a carbon chain length within the ranges of from $C_{11}$ to $C_{14}$, from $C_{14}$ to $C_{16}$, and from $C_{15}$ to $C_{18}$. Such suitable thioglycolic acid esters can be prepared by reacting a polyol of the above-mentioned type in the usual manner with thioglycolic acid at a molar ratio of from 1:1 to 1:n, n representing the number of hydroxyl groups of the polyol. Here, all hydroxyl groups of the polyol may be esterified with thioglycolic acid. However, according to the invention, preferably those thioglycolic acid esters which comprise an average of at most 3 thioglycolic acid radicals, and more preferably one or at most two thioglycolic acid radicals, per polyol molecule, are used.

When thioglycolates of monofunctional alcohols are used in component (e), the alcohol component of these esters consists of an aliphatic, linear or branched, primary, secondary, or tertiary alcohol with from 8 to 22 carbon atoms. Examples of possible alcohol components include alkanols such as n-octanol, n-dodecanol, n-hexadecanol, n-octadecanol, and, in particular, 2-ethylhexanol.

In the simplest case, component (e) consists of a polyol thioglycolic acid ester or a thioglycolic acid ester of a monofunctional alcohol. However, double and triple combinations of these groups of substances also may be used, and the components, in turn, may again be mixtures.

In a preferred form of the process of the invention, a pentaerythritol partial ester of fatty acids with from 8 to 22 carbon atoms at a molar ratio of pentaerythritol:fatty acid in the range from about 1:1 to 1:2 is worked into the molding mixtures based on polyvinyl chloride as component (d), and, as component (e), a thioglycolic acid ester of a monofunctional alcohol with from 8 to 18 carbon atoms, a monothioglycolic acid ester of aliphatic diols with from 2 to 6 carbon atoms, or a glycerylmonothioglycolate is employed.

The stabilizer combination used in the process according to the invention can be modified by additional co-stabilizers and adjuvants, depending on the intended use of the stabilized polyvinyl chloride molding mixtures. Such additives, known per se, can be used in the usual quantities, such as, for example, in quantities of from 0.1 to 20 parts by weight per 100 parts by weight of polyvinyl chloride resin compound.

For the stabilization of molding mixtures intended for the preparation of tubing and profiles in the extrusion method, from about 0.5 to 1 parts by weight of paraffin with a solidification point of from about 50° to 100° C. and/or free fatty acid with from 8 to 22 carbon atoms are, for example, worked in with the stabilizer mixture per 100 parts by weight of polyvinyl chloride. Suitable fatty acids are those mentioned above, palmitic and stearic acid being preferred.

Polyvinyl chloride molding mixtures for the production of hollowware by the extrusion blow method can contain, for example, from about 0.5 to 5 parts by weight of epoxidized soybean oil and from about 0.1 to 8 parts by weight of high-molecular ester wax per 100 parts by weight of polyvinyl chloride. Suitable highmolecular ester waxes include mineral waxes and paraffin oxidates and particularly complex esters of (i) aliphatic, cycloaliphatic and/or aromatic dicarboxylic acids with from 2 to 22 carbon atoms in the molecule;

(ii) aliphatic polyols with from 2 to 6 hydroxyl groups in the molecule; and (iii) aliphatic monocarboxylic acids with from 12 to 30 carbon atoms in the molecule, in which the molar ratio of components (i), (ii), and (iii) is approximately n:1:nm-2(n-1)

wherein n represents a whole number of from 2 to 11 and m represents the hydroxyl groups in the polyol. These mixed esters have hydroxyl and acid numbers in the range from 0 to about 15. They can be prepared by known methods, such as, for example, that described in German Pat. No. 19 07 768, incorporated herein by reference. Complex esters of adipic acid, pentaerythritol, and stearic acid in the above molar ratio, n representing a whole number of from 2 to 8, are preferably used.

In the use of polyvinyl chloride molding mixtures for the production of foils by the rolling calender method, from about 0.5 to 5 parts by weight of epoxidized soybean oil, from about 0.1 to 1 part by weight of the above-mentioned high-molecular ester wax, and from about 0.2 to 0.5 parts by weight of α-phenylindole or benzoylstearoyl methane are, for example, added as co-stabilizers, per 100 parts of polyvinyl chloride. In addition, from about 0.05 to 0.2 parts by weight of calcium soaps and from about 0.1 to 0.2 parts by weight of zinc soaps, per 100 parts by weight of polyvinyl chloride, result in completely adequate stabilization.

In a preferred form of the process according to the invention, the following are worked into molding mixtures for the production of tubing and profiles by the extrusion method, per 100 parts by weight polyvinyl chloride:

(a) from about 1 to 2 parts by weight sodium aluminosilicate;

(b) from about 0.8 to 1.2 parts by weight of one or more calcium salts of fatty acids;

(c) from about 0.1 to 0.4 parts by weight of one or more zinc salts of fatty acids;

(d) from about 0.3 to 0.5 parts by weight of a pentaerythritol partial ester of fatty acids;

(e) from about 0.2 to 0.5 parts by weight of thioglycolatic acid ester; and (f) from about 0.5 to 1 part by weight of paraffin and/or fatty acid.

The stabilizer mixtures according to the invention can be obtained by the simple, mechanical mixing of the components in conventional mixers. They are obtained in the form of flowing, dust-free products by this preparation.

The mixtures according to the invention provide a good stabilizing effect upon polyvinyl chloride and mixed polymer of vinyl chloride with a predominant polyvinyl chloride content. The mixed polymerization components in question are, in addition to vinyl esters like vinyl acetate, preferably acrylic acid esters and vinylidene chloride. The polymers and/or mixed polymers can be prepared by known processes, like suspension or block polymerization. Their K-value advantageously lies between about 35 and 80. The stabilization of such resin mixtures is also an aspect of the invention.

The polyvinyl chloride molding mixtures stabilized by the process according to the invention are used mainly for the production of tubing and profiles by the extrusion method, for the production of hollow packaging materials, and for the production of rolled foils. Articles of any desired shape are included within the scope of the invention.

The processing characteristics of the polyvinyl chloride molding mixtures stabilized with the aid of the process according to the invention are absolutely comparable to the characteristics of the polyvinyl chloride molding mixtures stabilized with heavy metals. This applies particularly to the initial color, the initial stability, and the reserve stability of the molding mixtures. Consequently, the stabilizer combination used in the process according to the invention is a perfect substitute for the heavy metal combinations used until now. The process according to the invention thus brings with it a considerable progress in the field of occupational physiology.

The following preparations and examples are illustrative of the practice of the invention without being limitative in any manner.

I. PREPARATIONS

The preparation of suitable sodium aluminosilicates

The silicate solution was added to the aluminate solution under vigorous agitation in a vessel having a capacity of 15 liters. Agitation was effected at 3000 r.p.m. by means of an agitator having a dispersing disc. The two solutions were at room temperature. An X-ray amorphous sodium aluminosilicate was formed as a primary product of precipitation with an exothermic reaction. After agitation for 10 minutes, the suspension of the precipitation product was transferred to a crystallizer and, for the purpose of crystallization, remained in the crystallizer for 6 hours at 90° C. under agitation (250 r.p.m.). The alkaline solution comprising the mother liquor was drawn off from the crystal sludge, and the filtration residue was washed with deionized water until the washing water flowing off had a pH value of approximately 10. Thereafter the washed filtration residue was dried as specified. The water contents were determined by heating the predried products to 800° C. for 1 hour. The sodium aluminosilicates, washed or neutralized to a pH value of approximately 10 and then dried, were subsequently ground in a ball mill. The grain size distribution was determined by means of a sedimentation balance.

The calcium binding power, i.e., complexing capacity, can be determined according to the Calcium Binding Power Test, which is as follows:

One liter of an aqueous solution containing 0.594 g of $CaCl_2$ (300 mg CaO/1=30° dH) (German hardness degrees) and standardized with dilute NaOH to a pH value of 10, is mixed with 1 g of the aluminosilicate, calculated as an anhydrous product. Then the suspension is stirred vigorously for 15 minutes at a temperature of 22° C. ($\pm$2° C.). After removal of the aluminosilicate by filtration, the residual hardness x of the filtrate is determined. The calcium binding power is calculated from this in mg of CaO/g of aluminosilicate according to the formula: (30-x)$\times$10.

When the calcium-binding capacity is determined at higher temperatures, for example, at 60° C., the resulting values are always better than at 22° C.

| Conditions for producing sodium aluminosilicate A: | |
| --- | --- |
| Precipitation: | 2.985 kg of aluminate solution of the composition: |
| | 17.7% $Na_2O$, 15.8% $Al_2O_3$, |
| | 66.6% $H_2O$ |
| | 0.15 kg of sodium hydroxide |
| | 9.420 kg of water |
| | 2.445 kg of a 25.8% sodium silicate solution of the composition |
| | 1 $Na_2O$ . 6.0 $SiO_2$ freshly prepared from a commercial sodium silicate and silicic acid that is readily soluble in alkali |
| Crystallization: | 6 hours at 90° C. |
| Drying: | 24 hours at 100° C. |
| Composition: | 0.9 $Na_2O$ . 1 $Al_2O_3$ . 2.04 $SiO_2$ |
| | 4.3 $H_2O$ (= 21.6% $H_2O$) |
| Degree of crystallization: | Fully crystalline |
| Calcium binding power: | 170 mg CaO/g active substance. |

The particle size distribution, determined by sedimentation analysis, resulted in a mixture range of the particle size distribution curve at 3 to 6 $\mu$.

The sodium aluminosilicate A exhibits the following interference lines in the X-ray diffraction graph:
d values, photographed with Cu-$K_\alpha$ radiation in Å

| |
| --- |
| 12.4 |
| 8.6 |
| 7.0 |
| 4.1 (+) |
| 3.68 (+) |
| 3.38 (+) |
| 3.26 (+) |
| 2.96 (+) |
| 2.73 (+) |
| 2.60 (+) |

It is quite possible that all these interference lines will not appear in the X-ray diffraction graph, particularly when the aluminosilicates are not fully crystallized.

Thus, the most important d values for characterizing these types have been characterized by a "($\pm$)".

| Conditions for producing sodium aluminosilicate B: | |
| --- | --- |
| Precipitation: | 7.63 kg of an aluminate solution of the composition 13.2% $Na_2O$; 8.0% $Al_2O_3$; 78.8% $H_2O$; |
| | 2.37 kg of a sodium silicate solution of the composition |
| | 8.0% $Na_2O$; 26.9% $SiO_2$; 65.1% $H_2O$; |
| Preparation ratio in mol: | 3.24 $Na_2O$; 1.0 $Al_2O_3$; 1.78 $SiO_2$; 70.3 $H_2O$; |
| Crystallization: | 6 hours at 90° C.; |
| Drying: | 24 hours at 100° C.; |
| Composition of the dried product | 0.99 $Na_2O$ . 1.00 $Al_2O_3$ . 1.83 $SiO_2$ 4.0 $H_2O$; (= 20.9% $H_2O$) |
| Crystalline form: | Cubic with greatly rounded corners and edges |
| Average particle diameter: | 5.4 $\mu$ |
| Calcium binding power: | 172 mg CaO/g active substance. |

| Conditions for producing sodium aluminosilicate C: | |
| --- | --- |
| Precipitation: | 12.15 kg of aluminate solution of the composition |
| | 14.5% $Na_2O$; 5.4% $Al_2O_3$; 80.1% $H_2O$; |
| | 2.37 kg of a sodium silicate solution of the composition |
| | 8.0% $Na_2O$; 26.9% $SiO_2$; 65.1% $H_2O$ |
| Preparation ratio in mol: | 5.0 $Na_2O$; 1.0 $Al_2O_3$; 2.0 $SiO_2$; 100 $H_2O$; |
| Crystallization: | 1 hour at 90° C.: |
| Drying: | Hot atomization of a suspension of the washed product (pH 10) at 295° C.; Content of solid substance in the suspension 46%; |
| Composition of the dried product: | 0.96 $Na_2O$ . 1 $Al_2O_3$ . 1.96 $SiO_2$ 4 $H_2O$; |
| Crystalline form: | Cubic with greatly rounded corners and edges; Water content 20.5%; |
| Average particle diameter: | 5.4 $\mu$ |
| Calcium binding power: | 172 mg CaO/g active substance. |
| All percentages given in the preceding examples are by weight. | |

II. EXAMPLES

The effect of the stabilizer combinations was tested with the "static thermostability" of rolled sheets in Examples 1 to 3 below. For this purpose, polyvinyl chloride molding mixtures (Heraeus FT 420 R) containing stabilizer mixtures were turned into test sheets on a laboratory rolling mill with the dimensions 450$\times$220 mm (by Berstorff) at a roller temperature of 170° C. and a roller rotation of 12.5 rpm, in synchronization, within a period of 5 minutes. The sheets, which had a thickness of approximately 0.5 mm, were cut into square test samples with a length of 10 mm for the edges and then exposed to a temperature of 180° C. in a drying chamber with 6 rotating shelves. Samples were removed at intervals of 15 minutes, and their changes in color were evaluated.

In the Tables 2, 4, and 5 below, the starting color is recorded as related to the stabilizer mixture added, followed by the time after which the test was concluded because of too much discoloration (loss of stability).

EXAMPLE 1

Polyvinyl chloride molding mixtures A to F, the compositions of which can be found in Table 1 below, were tested by the method described above.

Composition A was a PVC molding mixture stabilized according to the process of the invention, this composition being especially suitable for the production of tubing and profiles by the extrusion method. Compositions B to F were comparison molding mixtures corresponding to formulation A with the exception that some of the components were deleted or exchanged.

TABLE 1

| Component | \multicolumn{6}{c}{PVC Molding Mixture} |
|---|---|---|---|---|---|---|
| | A | B | C | D | E | F |
| Suspension-PVC (K-value 65) | 100 | 100 | 100 | 100 | 100 | 100 |
| Sodium aluminosilicate[1] | 2.0 | 2.0 | 2.0 | — | — | — |
| Calcium stearate | 1.0 | 1.0 | 1.0 | 1.0 | 1.0 | 1.0 |
| Zinc stearate | 0.3 | 0.3 | 0.3 | 0.3 | 0.3 | 0.3 |
| Pentaerythritol stearate[2] | 0.3 | — | 0.3 | 0.3 | 0.3 | — |
| Wax ester (type cetyl palmitate) | — | 0.3 | — | — | — | — |
| 2-Ethylhexyl thioglycolate | 0.3 | 0.3 | — | 0.3 | — | — |
| Paraffin M.p.: 71° C. | 0.75 | 0.75 | 0.75 | 0.75 | 0.75 | 0.75 |

[1]Synthetic zeolite NaA; $Na_2O:Al_2O_3:SiO_2 = 0.9:1:2.04$; water content: 21.6 percent by weight; particle size maximum: 3–6 μ
[2]Molar ratio pentaerythritol:stearic acid of 1:1.5; OH-number 212

The values determined for the "static thermostability" are set forth in the following table:

TABLE 2

| Molding mixture | Starting color | Loss of stability (minutes) |
|---|---|---|
| A | white | 135 |
| B | white | 105 |
| C | reddish | 120 |
| D | white | 45 |
| E | reddish | 45 |
| F | reddish | 30 |

EXAMPLE 2

Polyvinyl chloride molding mixtures G to L, the composition of which is shown below in Table 3, were tested according to the method given above.

The composition G was a polyvinyl chloride molding mixture stabilized by the process according to the invention, this composition being suitable for the manufacture of packaging materials, particularly for the production of bottles by the extrusion blow method. Comparison molding mixtures are identified as mixtures H to L, which corresponded to formulation G with the exception that some of the components were deleted or exchanged.

TABLE 3

| Component | \multicolumn{6}{c}{PVC Molding Mixture} |
|---|---|---|---|---|---|---|
| | G | H | I | J | K | L |
| Suspension-PVC (K-value 60) | 100 | 100 | 100 | 100 | 100 | 100 |
| Sodium aluminosilicate[1] | 1.0 | 1.0 | 1.0 | — | — | — |
| Calcium stearate | 0.5 | 0.5 | 0.5 | 0.5 | 0.5 | 0.5 |
| Zinc stearate | 0.3 | 0.3 | 0.3 | 0.3 | 0.3 | 0.3 |
| Pentaerythritol stearate[2] | 1.0 | — | 1.0 | 1.0 | 1.0 | — |
| Wax ester (type acetyl palmitate) | — | 1.0 | — | — | — | — |
| 2-Ethylhexyl thioglycolate | 0.3 | 0.3 | — | 0.3 | — | — |
| Epoxidized soybean oil[3] | 4.0 | 4.0 | 4.0 | 4.0 | 4.0 | 4.0 |
| Complex ester[4] | 0.5 | 0.5 | 0.5 | 0.5 | 0.5 | 0.5 |

[1]Synthetic zeolite NaA; $Na_2O:Al_2O_3:SiO_2 = 0.9:1:2.04$; water content 21.6 percent by weight; particle size maximum: 3–6 μ
[2]Molar ratio pentaerythritol:stearic acid of 1:1.5; OH-number 212
[3]Epoxide-number 6.3
[4]Adipic acid:pentaerythritol:stearate molar ratio of 6:7:16 OH-number approximately 2; acid-number approximately 10.

The values determined for the "static thermostability" of this test series are summarized in Table 4:

TABLE 4

| Molding mixtures | Starting color | Loss of Stability (minutes) |
|---|---|---|
| G | colorless | 180 |
| H | colorless | 150 |
| I | reddish | 180 |
| J | colorless | 105 |
| K | reddish | 105 |
| L | reddish | 60 |

EXAMPLE 3

A PVC molding mixture had the following composition:
100 parts by weight of suspension-PVC (K-value 60);
0.75 parts by weight of calcium stearate;
0.25 parts by weight of zinc stearate;
0.3 parts by weight of pentaerythritol stearate
(molar ratio of pentaerythritol:stearic acid of 1:1.5; OH-number 212);
0.3 parts by weight of 2-ethylhexyl thioglycolate; and
0.75 parts by weight of paraffin, M.p.: 70° C.

Molding mixtures N to S were prepared by adding to a molding mixture of formulation M, in portions, the following zeolites n to s in amounts of 1 part by weight per 100 parts by weight of polyvinyl chloride:

(n) synthetic, nonactivated Na-zeolite, type NaA;

$$Na_2O:Al_2O_3:SiO_2 = 0.99:1:1.82;$$

water content: 20.9 percent by weight;
mean particle size diameter: 5.4 μ;

(o) synthetic, nonactivated Na-zeolite, type NaX;

$$Na_2O:Al_2O_3:SiO_2 = 1:1:2.4-2.6;$$

(p) synthetic, nonactivated Na-zeolite, type NaY;

$$Na_2O:Al_2O_3:SiO_2 = 1:1:4.3;$$

(q) synthetic, nonactivated K-zeolite, type KA;

$$K_2O:Al_2O_3:SiO_2 = 1:1:2;$$

(r) synthetic, nonactivated Ca-zeolite, type CaA, prepared from (n) by ion exchange with calcium chloride, (s) synthetic, nonactivated sodium aluminosilicate, amorphous $Na_2O:Al_2O_3:SiO_2 = 1:1:2.$ The molding mixture N was stabilized by the process according to the invention. The molding mixtures M and O to Q are comparison mixtures obtained by elimination or exchange of the sodium aluminosilicate (n).

The molding mixtures M to S were tested for their "static thermostability" by the method described above. The results are summarized in the following table:

TABLE 5

| Molding Mixture | Zeolite | Starting Color | Loss of Stability (minutes) |
|---|---|---|---|
| M | — | white | 45 |
| N | (n) NaA | white | 90 |
| O | (o) NaX | white yellow tint | 45 |
| P | (p) NaY | white | 45 |
| Q | (q) KA | white | 60 |
| R | (r) CaA | white | 60 |
| S | (s) Na amorph. | white | 60 |

EXAMPLE 4

A fast mixer was used to mix 100 parts by weight of suspension-PVC (K-value 65) with 4.65 parts by weight of a stabilizer mixture of the following composition:

(a) 20 parts by weight of synthetic, nonactivated Na-zeolite, type NaA; $Na_2O:Al_2O_3:SiO_2=0.99:1:1.83$; water content: 20.9 percent by weight;

(b) 10 parts by weight of calcium stearate (c) 3 parts by weight of zinc stearate (d) 3 parts by weight of pentaerythritol stearic acid partial ester (molar ratio of 1:1.5; OH-number 212);

(e) 3 parts by weight of 2-ethylhexyl thioglycolate; and (f) 7.5 parts by weight of paraffin, M.p: 71° C. into a molding mixture. A commercial double reduction worm gear extruder CM 55 (manufacturer: Cincinnati-Milacron, Vienna) was used to process the molding mixture. The extruder has the following technical data:

| Worm gear diameter: | 55/110 mm |
|---|---|
| Effective length: | 1050 mm |
| Arrangement: | conical/combing |
| Direction of rotation: | opposite, diverging upward |

The following conditions were observed for the production of PVC-tubing with 5.3 mm wall thickness and 110 mm outside diameter:

| Cylinder: | 185/170/135° C. |
|---|---|
| Feeding: | 140° C. |
| Head: | 190/190° C. |
| Jet: | 200° C. |
| Cone: | 190° C. |
| Core: | 140° C. |
| Motor speed: | 2,000 rpm |
| Worm gear speed: | 35 rpm |
| Motor load: | 42–45% |
| Completely filled worm gear, output: | 157 kg/hr. |

The tubes obtained were white to caramel-colored.

EXAMPLE 5

A stabilizer combination was prepared from the following components:

(a) 10 parts by weight of synthetic, nonactivated Nazeolite; type NaA, $Na_2O:Al_2O_3:SiO_2=0.99:1:1.83$; water content: 20.9 percent by weight;

(b) 2 parts by weight of calcium stearate;

(c) 4 parts by weight of zinc octoate;

(d) 20 parts by weight of pentaerythritol stearate (molar ratio of 1:1.5; OH-number 212);

(e) 4 parts by weight of 2-ethylhexyl thioglycolate;

(f) 10 parts by weight of adipic acid/pentaerythritol stearate (molar ratio of 6:7:16; OH-number approximately 2; acid-number approximately 10); and (g) 80 parts by weight of epoxidized soybean oil (epoxide number 6.3).

Ninety-two parts by weight of suspension-PVC (K-value 60), 8 parts by weight of methacrylate-butadiene-styrene resin, and 7 parts by weight of the above stabilizer combination were mixed together in a fast mixer until a flowing dryblend composition was obtained, which was processed into bottles with a capacity of approximately 290 ml in conventional extrusion blow equipment (cylinder diameter 40 mm; relative worn gear length 20 D). Under constant operating conditions, this PVC-molding mixture produced bottles having good transparency, smooth and lustrous surface, and high toughness.

EXAMPLE 6

A stabilizer combination was prepared of the following components:

(a) 10 parts by weight of synthetic, nonactivated Nazeolite, type NaA; $Na_2O:Al_2O_3:SiO_2=0.99:1:1.83$; water content: 20.9 percent by weight;

(b) 6 parts by weight of calcium stearate;

(c) 5 parts by weight of zinc stearate;

(d) 24 parts by weight of pentaerythritol stearate (molar ratio of 1:1.5);

(e) 6 parts by weight of 2-ethylhexyl thioglycolate;

(f) 10 parts by weight of adipic acid/pentaerythritol stearate (molar ratio of 6:7:16; OH-number approximately 2; acid-number approximately 10)

(g) 3 parts by weight of β-phenylindole; and (h) 40 parts by weight of epoxidized soybean oil (epoxide-number 6.3).

One hundred parts by weight of suspension-PVC (K-value 60) and 7.35 parts by weight of the above stabilizer combination were mixed into a molding mixture in a fast mixer. This molding mixture was plasticized in the usual manner in a laboratory roller mill with the dimensions 450×200 mm (by Berstorff) at a roller temperature of 170° C. and a roller speed of 12.5 rpm in synchronization, and rolled out into a translucent foil approximately 0.5 mm thick. This foil had a smooth and lustrous surface.

EXAMPLE 7

A molding mixture was prepared in a fast mixer of 100 parts by weight of suspension-PVC (K-value 65) and 4.65 parts by weight of a stabilizer mixture having the following composition.

(a) 20 parts by weight of synthetic, nonactivated Nazeolite, type NaA: $Na_2O:Al_2O_3:SiO_2=0.99:1:1.83$; water content: 20.9 percent by weight;

(b) 10 parts by weight of calcium stearate;

(c) 3 parts by weight of zinc stearate;

(d) 2 parts by weight of glyceryl stearic acid partial ester (molar ratio of 1:1.5);

(e) 4 parts by weight of ethylene glycol monothioglycolate; and (f) 7.5 parts by weight of paraffin, M.p.: 71° C. A commercial double reduction worm gear extruder CM 55 (manufacturer: Cincinnati-Milacron, Vienna) was used to process the molding mixture. This extruder has the following technical data:

| | |
|---|---|
| Worm gear diameter: | 55/110 mm |
| Effective length: | 1050 mm |
| Arrangement: | conical/combing |
| Direction of rotation: | opposite, diverging upward |

The following conditions were observed for the production of PVC-tubing with 5.3 mm wall thickness and 110 mm outside diameter:

| | |
|---|---|
| Cylinder: | 185/170/135° C. |
| Feeding: | 140° C. |
| Head: | 190/190° C. |
| Jet: | 200° C. |
| Cone: | 190° C. |
| Core: | 140° C. |
| Motor speed: | 2,000 rpm |
| Worm gear speed: | 35 rpm |
| Motor load: | 42–45% |
| Completely filled worm gear, output: | 157 kg/hr. |

White to caramel-colored tubes were obtained.

EXAMPLE 8

A stabilizer combination was prepared from the following components:

(a) 10 parts by weight of synthetic, nonactivated Nazeolite, type NaA; $Na_2O:Al_2O_3SiO_2 = 0.99:1:1.83$; water content: 20.9 percent by weight;

(b) 2 parts by weight of calcium stearate, (c) 4 parts by weight of zinc octoate;

(d) 20 parts by weight of glyceryl di-12-hydroxystearate;

(e) 4 parts by weight of 1,10-decanediol dithioglycolate (f) 10 parts by weight of adipic acid/pentaerythritol stearate (molar ratio 6:7:16; OH-number approximately 2; acid-number approximately 10); and (g) 80 parts by weight of epoxidized soybean oil (epoxide-number 6.3). Ninety-two parts by weight of suspension-PVC (K-value 60), 8 parts by weight of methacrylate-butadiene-styrene resin, and 7 parts by weight of the above stabilizer combination were mixed to obtain a flowing dry-blend composition in a fast mixer, which was subsequently processed into bottles with a capacity of 290 ml in commercial extrusion blow equipment (cylinder diameter 40 mm; relative worm gear length 20 D). Under constant operating conditions, this PVC-molding mixture produced bottles having good transparency, smooth and lustrous surface, and great toughness.

EXAMPLE 9

A stabilizer combination was prepared from the following components:

(a) 10 parts by weight of synthetic, nonactivated Nazeolite, type NaA; $Na_2O:Al_2O_3:SiO_2=0.99:1:1.83$; water content: 20.9 percent by weight;

(b) 6 parts by weight of calcium stearate;

(c) 5 parts by weight of zinc stearate;

(d) 24 parts by weight of trimethylolpropane laurate (molar ratio of 1:1.5);

(e) 6 parts by weight of n-octadecyl thioglycolate;

(f) 10 parts by weight of adipic acid/pentaerythritol stearate (molar ratio of 6:7:16; OH-number approximately 2; acid-number approximately 10)

(g) 3 parts by weight of β-phenylindole; and (h) 40 parts by weight of epoxidized soybean oil (epoxide-number 6.3). One hundred parts by weight of suspension-PVC (K-value 60) and 7.35 parts by weight of the above stabilizer combination were mixed into a molding mixture on a fast mixer. This molding mixture was plasticized in the usual manner in a laboratory roller mill with the dimensions 450×220 mm (by Berstorff) at a roller temperature of 170° C. and a roller speed of 12.5 rpm in synchronization, and rolled out into a translucent foil approximately 0.5 mm thick. This foil showed a smooth and lustrous surface.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for stabilizing polyvinyl chloride molding mixtures, which comprises admixing
   (a) from about 0.2 to 5 parts by weight of a synthetic, crystalline sodium zeolite A of small particle size and containing from about 13 to 25 percent by weight of water of crystallization, which has the composition $$0.7-1.1Na_2O.Al_2O_3.1.3-2.4SiO_2$$

with respect to the anhydrous form;
   (b) from about 0.05 to 1.5 parts by weight of one or more calcium salts of fatty acids with from 8 to 22 carbon atoms;
   (c) from about 0.05 to 0.5 parts by weight of one or more zinc salts of fatty acids with from 8 to 22 carbon atoms;
   (d) from about 0.2 to 2.0 parts by weight of partial esters of polyols with from 2 to 6 carbon atoms and from 2 to 6 hydroxyl groups and fatty acids with from 8 to 22 carbon atoms, which contain an average of at least one free polyol-hydroxyl group per molecule and have an OH-number of from about 140 to 580; and
   (e) from about 0.1 to 10 parts by weight of thioglycolic acid esters of polyols with from 2 to 6 hydroxyl groups and/or thioglycolic acid esters of monofunctional alcohols with from 8 to 22 carbon atoms with 100 parts by weight of polyvinyl chloride or copolymer of vinyl chloride.

2. The process of claim 1, wherein a total of from about 1 to 100 parts by weight of components (a) to (e) are added per 100 parts by weight of polyvinyl chloride or copolymer of polyvinyl chloride.

3. The process of claim 1, wherein a total of from about 2 to 5 parts by weight of components (a) to (e) are added per 100 parts by weight of polyvinyl chloride of copolymer of vinyl chloride.

4. The process of claim 1, wherein the sodium zeolite A of component (a) has a particle size of from about 0.1 to 20μ.

5. The process of claim 1, wherein the sodium zeolite A of component (a) is a zeolite 4A containing water of crystallization with a water content of from about 18 to 25 percent by weight.

6. The process of claim 1, wherein component (d) comprises partial esters having an acid number less than about 15.

7. The process of claim 6, wherein the hydroxyl number is from about 170 to 540.

8. The process of claim 6, wherein the acid number is less than 8.

9. The process of claim 1, wherein component (e) comprises thioglycolates of aliphatic linear or branched monoalcohols and/or mono- and/or di-thioglycolates of said polyols.

10. The process of claim 1, wherein component (d) comprises a pentaerythritol partial ester of fatty acids having from 8 to 22 carbon atoms with a pentaerythritol to fatty acid molar ratio of from about 1:1 to 1:2 and component (e) comprises a thioglycolic acid ester of a monofunctional alcohol having from 8 to 18 carbon atoms, a monothioglycolic acid ester of aliphatic diols of from 2 to 6 carbon atoms, or a glyceryl monothioglycolate.

11. The process of claim 1 for stabilizing polyvinyl chloride molding mixtures to be used for the manufacture of tubing and profiles by extrusion method, wherein from about 0.5 to 1 part by weight of paraffin with a melting point of from about 50° to 110° C. and/or from about 0.5 to 1 part by weight of a fatty acid having from about 8 to 22 carbon atoms, is also admixed per 100 parts by weight of polyvinyl chloride or copolymer of vinyl chloride.

12. The process of claim 1 for stabilizing polyvinyl chloride molding mixtures to be used for the manufacture of hollowware by the extrusion blow method, wherein from about 0.5 to 5 parts by weight of epoxidized soybean oil and from about 0.1 to 0.8 parts by weight of high molecular ester wax, are also admixed per 100 parts by weight of polyvinyl chloride or copolymer of vinyl chloride.

13. The process of claim 1 for stabilizing polyvinyl molding mixtures to be used for the preparation of foils by the rolling calender method, wherein from about 0.5 to 5 parts by weight of epoxidized soybean oil, from about 0.1 to 1 part by weight of high-molecular ester wax, and 0.2 to 0.5 parts by weight of $\alpha$-phenylindole or benzoyl-stearoyl methane are also admixed per 100 parts by weight of polyvinyl chloride or copolymer of vinyl chloride.

14. The process of claim 11, wherein
(a) from about 1 to 2 parts by weight of said sodium zeolite A;
(b) from about 0.8 to 1.2 parts by weight of said calcium salt or salts;
(c) from about 0.1 to 0.4 parts by weight of said zinc salt or salts;
(d) from about 0.3 to 0.5 parts by weight of said partial esters;
(e) from about 0.2 to 0.5 parts by weight of said thioglycolic acid esters; and
(f) from about 0.5 to 1 part by weight of the paraffin, are admixed per 100 parts by weight of polyvinyl chloride or copolymer of vinyl chloride.

15. A stabilizer composition of polyvinyl chloride molding mixtures which comprises
(a) from about 4 to 100 parts by weight of a synthetic, crystalline sodium zeolite A of small particle size and containing from about 13 to 25 percent by weight of water of crystallization, which has the composition $$0.7-1.1 \ Na_2O.Al_2O_3.1.3-2.4 \ SiO_2$$

with respect to the anhydrous form;
(b) from about 1 to 30 parts by weight of one or more calcium salts of fatty acids with from 8 to 22 carbon atoms;
(c) from about 1 to 10 parts by weight of one or more zinc salts of fatty acids with from 8 to 22 carbon atoms;
(d) from about 4 to 40 parts by weight of partial esters of polyols with from 2 to 6 carbon atoms and from 2 to 6 hydroxyl groups and fatty acids with from 8 to 22 carbon atoms, which contain an average of at least one free polyol-hydroxyl group per molecule and have an OH-number of from about 140 to 580; and
(e) from about 2 to 20 parts by weight of thioglycolic acid esters of polyols with from 2 to 6 hydroxyl groups and/or thioglycolic acid esters of monofunctional alcohols with from 8 to 22 carbon atoms.

16. The stabilizer composition of claim 15, wherein the sodium zeolite A of component (a) has a particle size of from about 0.1 to 20 $\mu$.

17. The stabilizer composition of claim 15, wherein the sodium zeolite A of component (a) is a zeolite 4A containing water of crystallization with a water content of from about 18 to 25 percent by weight.

18. The stabilizer composition of claim 15, wherein component (d) comprises partial esters having an acid number less than about 15.

19. The stabilizer composition of claim 18, wherein the hydroxyl number is from about 150 to 540.

20. The stabilizer composition of claim 18, wherein the acid number is less than 8.

21. The stabilizer composition of claim 15, wherein component (e) comprises thioglycolates of aliphatic linear or branched monoalcohols and/or mono- and/or di-thioglycolates of said polyols.

22. The stabilizer composition of claim 15, wherein component (d) comprises a pentaerythritol partial ester of fatty acids having from 8 to 22 carbon atoms with a pentaerythritol:fatty acid molar ratio of from about 1:1 to 1:2 and component (e) comprises a thioglycolate of a monofunctional alcohol having from 8 to 18 carbon atoms, a monothioglycolate of aliphatic diols of from 2 to 6 carbon atoms, or a glyceryl monothioglycolate.

23. In a process for stabilizing polyvinyl chloride molding mixtures which comprises admixing a stabilizing amount of stabilizer with 100 parts by weight of polyvinyl chloride or copolymer of vinyl chloride the improvement consisting of using
(a) from about 0.2 to 5 parts by weight of a synthetic, crystalline sodium zeolite A of small particle size and containing from about 13 to 25 percent by weight of water of crystallization, which has the composition $$0.7-1.1 \ Na_2O.Al_2O_3.1.3-2.4 \ SiO_2$$

with respect to the anhydrous form;
(b) from about 0.05 to 1.5 parts by weight of one or more calcium salts of fatty acids with from 8 to 22 carbon atoms;
(c) from about 0.2 to 2.0 parts by weight of partial esters of polyols with from 2 to 6 carbon atoms and from 2 to 6 hydroxyl groups and fatty acids with from 8 to 22 carbon atoms, which contain an average of at least one free polyol-hydroxyl group per molecule and have an OH-number of from about 140 to 580; and (e) from about 0.1 to 10 parts by weight of polyols with from 2 to 6 hydroxyl groups and/or thioglycolic acid esters of such polyols and/or thioglycolis acid esters of monofunctional alcohols with from 8 to 22 carbon atoms for said stabilizer.

24. A molding mixture having a polymer with a preponderant content of vinyl chloride units which comprises a stabilizing amount of a stabilizer composition of claim 15.

25. The molding mixture of claim 24 wherein heavy-metal containing stabilizers are absent.

26. The stabilizer composition of claim 15 which comprises from about 5 to 20 parts by weight of component (a);
from about 2 to 10 parts by weight of component (b);
from about 1 to 5 parts by weight of component (c);
from about 3 to 10 parts by weight of component (d); and
from about 1 to 5 parts by weight of component (e).

* * * * *